US012312312B2

United States Patent
Breuil et al.

(10) Patent No.: US 12,312,312 B2
(45) Date of Patent: May 27, 2025

(54) PROCESS FOR SEPARATING OUT AN EFFLUENT OBTAINED FROM AN OLIGOMERIZATION STEP

(71) Applicant: IFP Energies Nouvelles, Rueil-Malmaison (FR)

(72) Inventors: Pierre-Alain Breuil, Rueil-Malmaison (FR); Nicolas Aribert, Rueil-Malmaison (FR); Olivier Cotte, Rueil-Malmaison (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 213 days.

(21) Appl. No.: 17/779,278

(22) PCT Filed: Nov. 17, 2020

(86) PCT No.: PCT/EP2020/082321
§ 371 (c)(1),
(2) Date: May 24, 2022

(87) PCT Pub. No.: WO2021/104924
PCT Pub. Date: Jun. 3, 2021

(65) Prior Publication Data
US 2022/0402839 A1    Dec. 22, 2022

(30) Foreign Application Priority Data

Nov. 26, 2019 (FR) ...................... 1913245

(51) Int. Cl.
*B01D 3/06* (2006.01)
*B01D 3/14* (2006.01)
*B01D 3/34* (2006.01)
*B01D 5/00* (2006.01)
*B01J 31/14* (2006.01)
*B01J 31/22* (2006.01)
*B01J 31/24* (2006.01)
*C07C 7/00* (2006.01)
*C07C 7/04* (2006.01)
*C07C 7/148* (2006.01)
*C08F 6/02* (2006.01)
*C08F 6/10* (2006.01)
*C08F 6/04* (2006.01)

(52) U.S. Cl.
CPC ............. *C07C 7/005* (2013.01); *B01D 3/06* (2013.01); *B01D 3/148* (2013.01); *B01D 3/34* (2013.01); *B01D 5/006* (2013.01); *B01J 31/143* (2013.01); *B01J 31/22* (2013.01); *B01J 31/2404* (2013.01); *C07C 7/04* (2013.01); *C07C 7/14891* (2013.01); *C08F 6/02* (2013.01); *C08F 6/10* (2013.01); *C07C 2531/12* (2013.01); *C07C 2531/14* (2013.01); *C07C 2531/24* (2013.01); *C08F 6/04* (2013.01)

(58) Field of Classification Search
CPC .................................. C07C 7/005–08
See application file for complete search history.

(56) References Cited

U.S. PATENT DOCUMENTS

| | | | | |
|---|---|---|---|---|
| 3,073,812 A * | 1/1963 | Henderson | ............. | C08F 10/00 159/DIG. 10 |
| 3,245,967 A * | 4/1966 | Moon | ............. | C08F 6/02 528/483 |
| 3,321,546 A * | 5/1967 | Roest | ............. | B01J 31/0225 585/512 |
| 7,199,163 B2 * | 4/2007 | Bigiavi | ............. | C08F 6/003 585/329 |
| 8,153,757 B2 * | 4/2012 | Arich de Finetti | ..... | C08F 6/003 526/943 |
| 8,748,522 B2 * | 6/2014 | Spataro | ............. | B01J 8/20 526/348.6 |
| 8,816,147 B2 * | 8/2014 | Vinel | ............. | C07C 7/005 585/502 |
| 9,018,328 B2 * | 4/2015 | Jog | ............. | C08F 10/02 526/348 |
| 10,370,307 B2 | 8/2019 | Boutrot et al. | | |
| 2014/0012059 A1 * | 1/2014 | Vinel | ............. | C07C 7/04 585/809 |
| 2018/0179122 A1 | 6/2018 | Boutrot et al. | | |
| 2022/0127210 A1 * | 4/2022 | Arkatov | ............. | C07C 2/32 |

FOREIGN PATENT DOCUMENTS

FR    3061034 A1    6/2018
WO    01/47839 A1    7/2001

OTHER PUBLICATIONS

Speight, James G.. (2019). Handbook of Petrochemical Processes—7.4.2.6 Dimerization. (pp. 312). Taylor & Francis. Retrieved from https://app.knovel.com/hotlink/pdf/id:kt012G7133/handbook-petrochemical/dimerization.*
International Search Report dated Jan. 25, 2021 issued in corresponding PCT/EP2020/082321 application (2 pages).

* cited by examiner

*Primary Examiner* — Jonathan Luke Pilcher
(74) *Attorney, Agent, or Firm* — Csaba Henter; MILLEN, WHITE, ZELANO & BRANIGAN, P.C.

(57) ABSTRACT

The present invention relates to a process for treating an effluent obtained from an oligomerization step in a vaporization step. In particular, the oligomerization step is a step for dimerization of ethylene to 1-butene with a nickel-based catalytic system.

20 Claims, No Drawings

PROCESS FOR SEPARATING OUT AN EFFLUENT OBTAINED FROM AN OLIGOMERIZATION STEP

FIELD OF THE INVENTION

The present invention relates to a process for treating an effluent obtained from an oligomerization step in a vaporization step. In particular, the oligomerization step is a step for dimerization of ethylene to 1-butene with a nickel-based catalytic system.

PRIOR ART

The transformation of light olefins by means of a homogeneous catalyst based on a transition metal, in particular based on nickel, combined with a halogenated activator, for example an alkylaluminium chloride, has been studied since the 1950s. This research has led to the development and marketing of various processes.

For example, octenes or hexenes or nonenes are produced, respectively, by dimerization of butenes or oligomerization of propylene via the Dimersol™ process from Axens (Revue de l'Institut Français du Pétrole, Vol. 37, No. 5, September-October 1982, page 639). Octenes may be transformed in good yields by hydroformylation reaction followed by hydrogenation to isononanols. These C9 alcohols (i.e. alcohols comprising 9 carbon atoms) are notably used for the synthesis of phthalate-type plasticizers for PVC. Hexenes or nonenes may also be used as base for fuel with a very good octane number.

The development of catalytic systems capable of dimerizing olefins proceeds via the choice of the appropriate transition metal and ligands. Among the existing catalytic systems, several nickel-based catalytic systems using various ligands have been developed. Examples that may notably be mentioned include complexes of π-allyl nickel phosphine halides with Lewis acids, as described in French patent FR1410430B, complexes of nickel phosphine halides with Lewis acids, as described in U.S. Pat. No. 3,485,881A, complexes of nickel with imino-imidazole ligands as described in French patent FR2979836B, and nickel carboxylates with hydrocarbylaluminium halides, as described in U.S. Pat. No. 3,321,546A. In dimerization processes using such catalysts, it proves to be necessary to neutralize the catalyst at the end of the reaction in order to prevent the reaction from continuing undesirably.

Patent FR2733497 describes a process for producing 1-butene involving a separation zone in which the reaction effluent is vaporized in two steps by means of a vaporiser used at identical pressures followed by a step of vaporization using a thin-film evaporator.

Patent FR2992962B describes a process for producing and separating 1-hexene from a mixture of products obtained from an ethylene trimerization zone. In particular, said patent describes a separation zone using a series of staged flashes vaporizing the liquid effluent along an increasing temperature gradient ranging from 150-200° C. to 160-220° C.

In its studies, the Applicant Company has developed a novel process for separating out a neutralized oligomerization effluent using at least two vaporization steps along a decreasing pressure gradient.

Advantageously, the process according to the invention makes it possible to remove the neutralized catalyst by vaporization at a moderate temperature. Advantageously, the use of at least two vaporization steps at moderate temperature along a decreasing pressure gradient prevents the phenomenon of regain of activity of the neutralized catalyst, which is responsible for a reduction in selectivity towards the desired olefins. Thus, the process according to the invention makes it possible to maximize the production of desired olefins. The process according to the invention also makes it possible to limit the costs associated with the maintenance of the production units.

SUMMARY OF THE INVENTION

The present invention relates to a process for treating an effluent obtained from an oligomerization step, comprising a step of neutralizing to deactivate a catalytic composition said effluent followed by a step of thermal separation of the neutralized effluent, comprising a first vaporization step performed at a pressure of between 2.0 and 5.0 MPa and at a temperature of between 70 and 150° C., to obtain a liquid fraction sent to a second vaporization step, and a gas fraction, preferably sent to a distillation section, said second vaporization step is performed at a pressure of between 0.5 and 3.0 MPa and at a temperature of between 70 and 150° C., to obtain a liquid fraction and a gas fraction; preferably, said gas fraction is sent to the distillation section, in which the pressure of the first vaporization step is higher than the pressure of the second vaporization step, preferably by at least 0.5 MPa, preferably by at least 1.0 MPa, preferably by at least 1.5 MPa.

Thus, the thermal separation step of the process according to the invention makes it possible to remove the neutralized catalyst by vaporization at a moderate temperature. Advantageously, the use of at least two vaporization steps at moderate temperature along a decreasing pressure gradient prevents the phenomenon of regain of activity of the neutralized catalyst, which is responsible for a reduction in selectivity towards the desired olefins.

Another advantage of the process according to the invention is that it maximizes the selectivity towards 1-butene.

In a preferred embodiment, the first vaporization step is performed at a pressure of between 2.0 MPa and 4.5 MPa, preferably between 2.5 MPa and 4.0 MPa, and at a temperature of between 80° C. and 140° C., preferably between 90° C. and 130° C.

In a preferred embodiment, the second vaporization step is performed at a pressure of between 0.8 MPa and 3.0 MPa, preferably between 1.0 MPa and 2.0 MPa, and at a temperature of between 80° C. and 140° C., preferably between 90° C. and 130° C.

In a preferred embodiment, the thermal separation step involves a third vaporization step into which the liquid fraction obtained from the second vaporization step is sent, said third vaporization step is performed at a pressure of between 0.1 and 1.5 MPa and at a temperature of between 70 and 200° C., to obtain a liquid fraction and a gas fraction; preferably, said gas fraction is sent to the distillation section, and the pressure of the second vaporization step is higher than the pressure of the third vaporization step, preferably by at least 0.5 MPa, preferably by at least 0.8 MPa.

Preferably, the third vaporization step is performed at a pressure of between 0.3 and 1.2 MPa, preferably between 0.4 and 1.0 MPa, and at a temperature of between 80 and 140° C., preferably between 80 and 130° C.

In a preferred embodiment, the first step and/or the second step and/or the third step of thermal separation are performed by means of a flash vessel, preferably coupled with a heat exchanger.

In a preferred embodiment, the gas fraction obtained from the first vaporization step and/or the gas fraction obtained from the second vaporization step and/or the gas fraction obtained from the third vaporization step are liquefied by reducing the temperature, so as to reach a pressure of between 2.0 and 5.0 MPa and preferably to be sent to the distillation section.

In a preferred embodiment, the temperature for liquefying the gas fraction(s) obtained from the vaporization steps is between 0 and 60° C.

In a preferred embodiment, the oligomerization step uses a catalytic composition comprising an alkylaluminium halide and optionally a nickel precursor.

In a preferred embodiment, the alkylaluminium halide corresponds to the formula $[Al_m R^5{}_n X_{3-n}]_o$ in which
- $R^5$ is a linear or branched alkyl group, containing from 1 to 12 carbon atoms,
- X is a chlorine or bromine atom, and preferably a chlorine atom, and
- m is chosen from 1 and 2,
- n is chosen from 0, 1 and 2,
- o is chosen from 1 and 2.

In a preferred embodiment, the effluent obtained from the oligomerization step has a content of alkylaluminium halide of between 0.01 and 100 000 ppm by weight.

In a preferred embodiment, the step of neutralization of the effluent obtained from the oligomerization step is performed to deactivate a catalytic composition by placing said effluent in contact with a neutralizing system comprising:
- an alcohol of general formula $R^1OH$, in which the group $R^1$ is chosen from:
  - a linear or branched alkyl group containing from 2 to 20 carbon atoms,
  - an aryl group containing from 5 to 30 carbon atoms, and/or
- an amine of general formula $NR^2R^3R^4$, in which the groups $R^2$, $R^3$ and $R^4$, which may be identical or different, are chosen independently from:
  - a hydrogen,
  - a linear or branched alkyl group containing from 1 to 20 carbon atoms and optionally substituted with an $NH_2$ group.

In a preferred embodiment, the temperature at which the neutralizing system is placed in contact with the effluent obtained from the oligomerization step is that at which said oligomerization step takes place.

In a preferred embodiment, the neutralizing system comprises an alcohol of general formula $R^1OH$ and an amine of general formula $NR^2R^3R^4$.

In a preferred embodiment, the mole ratio of the amine to the alcohol is between 0.5 and 100.

DETAILED DESCRIPTION OF THE INVENTION

It is specified that, throughout this description, the expression "between . . . and . . . " should be understood as including the limits mentioned.

For the purposes of the present invention, the various embodiments presented may be used alone or in combination with each other, without any limit to the combinations.

For the purposes of the present invention, the various ranges of parameters for a given step, such as the pressure ranges and the temperature ranges, may be used alone or in combination. For example, for the purposes of the present invention, a preferred range of pressure values can be combined with a more preferred range of temperature values.

The present invention relates to a process for treating an effluent obtained, preferably directly, from an oligomerization step, comprising a step of neutralizing said effluent followed, preferably directly, by a step of thermal separation of the neutralized effluent, comprising:
- a first vaporization step performed at a pressure of between 2.0 and 5.0 MPa and at a temperature of between 70 and 150° C.; the liquid fraction obtained on conclusion of the first vaporization step is sent to a second vaporization step, and the gas fraction is sent to a distillation section,
- said second vaporization step is performed at a pressure of between 0.5 and 3.0 MPa and at a temperature of between 70 and 150° C.; the gas fraction obtained from the second vaporization step is sent to the distillation section,
- in which the pressure of the first vaporization step is higher than the pressure of the second vaporization step, preferably by at least 0.5 MPa, preferably by at least 1.0 MPa, preferably by at least 1.5 MPa.

Thus, the thermal separation step according to the invention makes it possible to remove the neutralized catalyst by vaporization at a moderate temperature. Advantageously, the use of at least two vaporization steps at moderate temperature along a decreasing pressure gradient prevents the phenomenon of regain of activity of the neutralized catalyst, which is responsible for a reduction in selectivity towards the desired olefins.

Another advantage of the neutralization process according to the invention is that it maximizes the selectivity towards 1-butene.

Thermal Separation Step

The process according to the invention thus comprises a thermal separation step, commonly known as vaporization, of an effluent, which has been neutralized beforehand to deactivate a catalytic composition, obtained from an oligomerization step, said thermal separation step comprising:
- a first vaporization step performed at a pressure of between 2.0 and 5.0 MPa and at a temperature of between 70 and 150° C., to obtain a liquid fraction sent to a second vaporization step, and a gas fraction, preferably sent to a distillation section,
- said second vaporization step is performed at a pressure of between 0.5 and 3.0 MPa and at a temperature of between 70 and 150° C., to obtain a liquid fraction and a gas fraction; preferably, said gas fraction is sent to the distillation section,
- in which the pressure of the first vaporization step is higher than the pressure of the second vaporization step, preferably by at least 0.5 MPa, preferably by at least 1.0 MPa, preferably by at least 1.5 MPa.

Said thermal separation step advantageously makes it possible to remove the neutralized catalyst and also the heavy (C12+) byproducts generated during the oligomerization step, and to send the desired olefins to a distillation section in order to purify them.

Preferably, the neutralized catalyst and the heavy (C12+) byproducts separated out in the vaporization step and contained in the liquid fraction obtained from the last vaporization step performed are sent to an incinerator.

The gas fractions sent to the distillation section comprise unconverted ethylene, the products formed during the oligomerization step and possibly solvent.

Thus, the thermal separation step according to the invention makes it possible to remove the neutralized catalyst by vaporization at a moderate temperature. Advantageously, the use of at least two vaporization steps at moderate temperature along a decreasing pressure gradient prevents the phenomenon of regain of activity of the neutralized catalyst, which is responsible for a reduction in selectivity towards the desired olefins.

Another advantage of the neutralization process according to the invention is that it maximizes the selectivity towards 1-butene.

Advantageously, the first vaporization step is performed at a pressure of between 2.0 and 5.0 MPa, preferably between 2.2 and 4.5 MPa, preferentially between 2.4 and 4.0 MPa and preferably between 2.5 and 3.5 MPa, at a temperature of between 70 and 150° C., between 80 and 140° C., preferably between 90 and 130° C. and preferably between 95 and 120° C.

Advantageously, the second vaporization step is performed at a pressure of between 0.5 and 3.0 MPa, preferably between 0.8 and 3.0 MPa, preferentially between 1.0 and 2.0 MPa, preferably between 1.1 and 1.8 MPa and very preferably between 1.2 and 1.5 MPa, and at a temperature of between 70 and 150° C., preferably between 80 and 140° C., preferentially between 90 and 130° C. and preferably between 95 and 125° C.

Preferably, the thermal separation step involves a third vaporization step into which the liquid fraction obtained from the second vaporization step is sent, said third vaporization step is performed at a pressure of between 0.1 and 1.5 MPa and at a temperature of between 70 and 150° C. The third vaporization step makes it possible to obtain a liquid fraction and a gas fraction; preferably, said gas fraction is sent to the distillation section.

In this case, the pressure of the second vaporization step is higher than the pressure of the third vaporization step, preferably by at least 0.5 MPa, preferably by at least 0.8 MPa, preferably by at least 1.0 MPa and preferably by at least 1.5 MPa.

The final liquid fraction obtained on conclusion of the final vaporization step, i.e. the second or the third vaporization step, is preferably sent to an incinerator, and the gas fraction obtained on conclusion of the final vaporization step, i.e. the second or the third vaporization step, is sent to the distillation section.

Advantageously, the third vaporization step is performed at a pressure of between 0.1 and 1.5 MPa, preferably between 0.3 and 1.2 MPa, preferentially between 0.4 and 1.0 MPa and preferably between 0.5 and 0.8 MPa, and at a temperature of between 70 and 150° C., preferably between 80 and 140° C., preferentially between 80 and 130° C., preferably between 85 and 130° C., preferably between 90 and 120° C. and very preferably between 95 and 110° C.

The term "flash" means gas/liquid separation performed by means of a pressure and/or temperature change.

Preferably, the first step and/or the second step and/or the third step of thermal separation are performed by means of a flash vessel, preferably coupled with a heat exchanger or any other sequence for partially vaporizing an effluent.

Thus, a wide choice of technologies is available for performing any of the thermal separation steps; preferably, said technologies are chosen from:
simple evaporators (or natural convection) with a jacket, with coils or of thermosiphon type,
more complex evaporators containing horizontal tubes, vertical tubes (for example of "rising film" or "falling film" type) or inclined tubes, with forced recirculation, and
more specific thin-film evaporator systems (vertical conical, horizontal conical, short-path) optionally coupled with various heating modes (steam, oils, molten salts, induction or the like), plate evaporators.

In a preferred embodiment, the thermal separation step does not involve thin-film evaporators as described in patent FR2733497.

In a preferred embodiment, the gas fraction obtained from the first vaporization step and/or the gas fraction obtained from the second vaporization step and/or the gas fraction obtained from the third vaporization step are liquefied upstream of said distillation section, by reducing the temperature, so as to reach a pressure of between 2.0 and 5.0 MPa and preferably to be sent to the distillation section, preferably by means of a pump. Advantageously, this embodiment makes it possible to dispense with the use of a compressor, which makes it possible to limit the operating costs of the process for treating the effluent obtained from an oligomerization step. Preferably, the temperature for liquefying the gas fraction(s) obtained from the vaporization steps is between 0 and 60° C., preferably between 10 and 55° C. and preferably between 20 and 50° C.

Neutralization Step

The process according to the invention comprises a step of neutralizing the effluent obtained from the oligomerization step. Preferably, the neutralization step involves placing said effluent in contact with a neutralizing system comprising, preferably consisting of:
an alcohol of general formula $R^1OH$, in which the group $R^1$ is chosen from:
a linear or branched alkyl group containing from 2 to 20 carbon atoms,
an aryl group containing from 5 to 30 carbon atoms, and/or
an amine of general formula $NR^2R^3R^4$, in which the groups $R^2$, $R^3$ and $R^4$, which may be identical or different, are chosen independently from:
a hydrogen,
a linear or branched alkyl group containing from 1 to 20 carbon atoms and optionally substituted with an $NH_2$ group.

Thus, said neutralization step makes it possible to obtain an effluent in which the catalytic composition is neutralized, i.e. deactivated. In other words, said composition no longer has any catalytic activity for the oligomerization reaction.

Advantageously, the group $R^1$ may be an alkyl group containing from 3 to 15 carbon atoms, preferably from 4 to 14 carbon atoms, preferably from 6 to 12 carbon atoms, and preferably between 7 and 10 carbon atoms.

In a preferred embodiment, the group $R^1$ is a branched alkyl.

In another preferred embodiment, the group $R^1$ is a linear alkyl.

In a preferred embodiment, the group $R^1$ is an alkyl substituted with one or more substituents chosen from a hydroxyl (—OH) and an amine (—$NH_2$).

Advantageously, the group $R^1$ may be an aryl group containing from 5 to 30 carbon atoms, preferably from 5 to 20 carbon atoms, preferably from 6 to 18 carbon atoms, and preferably from 6 to 15 carbon atoms.

Preferably, the alcohol of general formula $R^1OH$ is chosen from 1-propanol, 2-propanol, isopropanol, 1-butanol, 2-butanol, isobutanol, sec-butanol, tert-butanol, 1-pentanol, 2-pentanol, 3-pentanol, 1-hexanol, 2-hexanol, 3-hexanol, 1-heptanol, 2-heptanol, 3-heptanol, 4-heptanol, 1-octanol, 2-octanol, 3-octanol, 4-octanol, 2-ethyl-1-hexanol, 2-methyl-3-heptanol, 1-decanol, 2-decanol, 3-decanol, 4-decanol, 5-decanol, 1-undecanol, 2-undecanol, 7-methyl-2-decanol, 1-docecanol, 2-dodecanol, 2-ethyl-1-decanol, phenol, 2-methylphenol, 2,6-dimethylphenol, 2,4,6-trimethylphenol, 4-methylphenol, 2-phenylphenol, 2,6-diphenylphenol, 2,4,6-triphenylphenol, 4-phenylphenol, 2-tert-butyl-6-phenylphenol, 2,4-di-tert-butyl-6-phenylphenol, 2,6-diisopropylphenol, 2,6-di-tert-butylphenol and 4-methyl-2,6-di-tert-butylphenol, taken alone or as a mixture. Preferably, the alcohol of general formula $R^1OH$ is 2-ethyl-1-hexanol.

Preferably, the groups $R^2$, $R^3$ and $R^4$, which may be identical or different, are independently chosen from hydrogen, a linear or branched alkyl group containing from 2 to 20 carbon atoms, preferably from 4 to 14 carbon atoms, preferably from 6 to 12 carbon atoms and preferably from 7 to 10 carbon atoms.

In a preferred embodiment, at least one of the groups $R^2$, $R^3$ and $R^4$ is chosen from hydrogen.

In an even more preferred embodiment, at least two of the groups $R^2$, $R^3$ and $R^4$ are chosen from hydrogen.

In a particular embodiment, the amine is a polyamine such as a diamine. In other words, at least one of the groups $R^2$, $R^3$ and $R^4$ is substituted with an amino group (—$NH_2$). Preferably, one of the groups $R^2$, $R^3$ and $R^4$ is substituted with an amino group (—$NH_2$).

Preferably, the amine of general formula $NR^2R^3R^4$ is chosen from 1-propylamine, 2-propylamine, isopropylamine, 1-butylamine, 2-butylamine, isobutylamine, sec-butylamine, tert-butylamine, 1-pentylamine, 2-pentylamine, 3-pentylamine, 1-hexylamine, 2-hexylamine, 3-hexylamine, 1-heptylamine, 2-heptylamine, 3-heptylamine, 4-heptylamine, 1-octylamine, 2-octylamine, 3-octylamine, 4-octylamine, 2-ethyl-1-hexylamine, 2-methyl-3-heptylamine, 1-decylamine, 2-decylamine, 3-decylamine, 4-decylamine, 5-decylamine, 1-undecylamine, 2-undecylamine, 7-methyl-2-decylamine, 1-dodecylamine, 2-dodecylamine and 2-ethyl-1-decylamine, taken alone or as a mixture.

In a preferred embodiment, the neutralizing system comprises an alcohol of general formula $R^1OH$ and an amine of general formula $NR^2R^3R^4$.

Advantageously, the use of an alcohol $R^1OH$ and of an amine $NR^2R^3R^4$ as neutralizing system makes it possible to deactivate the catalytic composition, overcoming the problems associated with the corrosion and the regain of activity of said system, entailing a reduction in selectivity.

Specifically, the use of an alcohol and of an amine makes it possible synergistically to prevent the regain in activity of the neutralized catalytic composition during subsequent steps of purification of the effluent while at the same time limiting the corrosion associated with the presence of the spent catalytic composition.

When the neutralizing system comprises an alcohol and an amine, the effluent obtained from the oligomerization step is placed in contact, in one embodiment, successively with the amine and then with the alcohol.

In another embodiment, the effluent obtained from the oligomerization step is advantageously placed in contact with a mixture of alcohol and of amine.

In another embodiment, the effluent obtained from the oligomerization step is advantageously placed in contact simultaneously with an alcohol of formula $R^1OH$ and with an amine of formula $NR^2R^3R^4$.

Advantageously, the mole ratio of the amine to the alcohol is between 0.5 and 100, preferably between 1.0 and 90, preferably between 1.1 and 80, preferably between 1.5 and 70, preferably between 2.0 and 60, and preferably between 2.2 and 50. In a preferred embodiment, the mole ratio of the amine to the alcohol is between 0.5 and 40, preferably between 1.0 and 30, preferably between 1.1 and 20, preferably between 1.5 and 15, preferably between 2.0 and 10 and preferably between 2.2 and 5.0.

Advantageously, the mole ratio of the neutralizing system to the alkylaluminium halide is between 0.5 and 100, preferably between 1.0 and 90, preferably between 1.5 and 80, preferably between 2.0 and 70, preferably between 3.0 and 60, and preferably between 3.5 and 50. In a preferred embodiment, the mole ratio of the neutralizing system to the alkylaluminium halide is between 0.5 and 50, preferably between 1.0 and 40, preferably between 1.5 and 30, preferably between 2.0 and 20, preferably between 3.0 and 15, and preferably between 3.5 and 10.0.

Preferably, the effluent obtained directly from an oligomerization step has an alkylaluminium halide content of between 0.01 and 100 000 ppm by weight, preferably between 0.1 and 10 000 ppm by weight, preferably between 1.0 and 1000 ppm by weight, preferably between 2.0 and 600 ppm by weight, preferably between 3.0 and 400 ppm by weight, preferably between 5.0 and 200 ppm by weight, preferably between 6.0 and 100 ppm by weight, preferably between 8.0 and 50 ppm by weight, preferably between 10 and 40 ppm by weight and more preferably between 12 and 30 ppm weight relative to the total weight of said effluent.

Preferentially, the effluent obtained directly from an oligomerization step has an alkylaluminium chloride content such that the chlorine content is between 0.1 and 100 000 ppm by weight, preferably between 1.0 and 10 000 ppm by weight, preferably between 2.0 and 1000 ppm by weight, preferably between 3.0 and 600 ppm by weight, preferably between 4.0 and 400 ppm by weight, preferably between 5.0 and 200 ppm by weight, preferably between 8.0 and 100 ppm by weight, preferably between 10 and 80 ppm by weight, preferably between 12 and 70 ppm by weight and more preferably between 15 and 60 ppm weight relative to the total weight of said effluent.

The neutralizing system is preferably placed in contact with the effluent obtained from the oligomerization step at a temperature of between −40 and 250° C., preferably between −20° C. and 150° C., preferably between 20° C. and 100° C., preferably between 30 and 80° C. and very preferably between 40 and 60° C. Advantageously, the temperature at which the neutralizing system is placed in contact with the effluent obtained from the oligomerization step is that at which said oligomerization step takes place.

Advantageously, the alcohol of general formula $R^1OH$ and/or the amine of general formula $NR^2R^3R^4$ may be used in an identical or different solvent. Said solvent may be chosen from any solvent that is capable of diluting or dissolving the amine and/or the alcohol.

Advantageously, said solvent may be chosen from one or more solvents as described above for the catalytic composition.

"Optional" Oligomerization Step

Advantageously, the effluent treated in the process according to the invention is obtained on conclusion of an oligomerization step, preferably of ethylene to olefin using a catalytic composition comprising an alkylaluminium halide, and preferably a metal precursor, in particular a nickel precursor, said step allowing the production of said effluent treated in the process according to the invention, preferably in liquid form and comprising unconverted ethylene, the products formed during the oligomerization step, said catalytic composition and optionally solvent.

Preferably, the olefins obtained on conclusion of the oligomerization step are 1-butene, 2-butene, 1-hexene and/or 1-octene, alone or as a mixture.

The oligomerization step is preferably performed in the presence of said catalytic composition preferably comprising alkylaluminium halide and a nickel precursor, with a nickel concentration advantageously between $10^{-12}$ and 1.0 mol/L and preferably between $10^{-9}$ and 0.4 mol/L.

Advantageously, the oligomerization step is performed at a pressure of between 0.1 and 20.0 MPa, preferably between 0.1 and 15.0 MPa and preferably between 0.5 and 8.0 MPa, and at a temperature of between −40 and 250° C., preferably between −20 and 150° C., preferably between 20° C. and 100° C. and preferably between 30 and 80° C.

Preferably, the oligomerization step is a step of dimerization of ethylene to 1-butene and/or to 2-butene, a trimerization of ethylene to 1-hexene, or a tetramerization of ethylene to 1-octene.

Advantageously, the oligomerization step may be performed continuously or batchwise.

In a preferred embodiment, the constituents of the catalytic composition are injected into a stirred reactor by conventional mechanical means or by external recirculation, in which the olefin reacts, preferably with temperature control. In another embodiment, the alkylaluminium halide and a solution comprising the nickel precursor and optionally a ligand are injected into a stirred reactor by conventional mechanical means or by external recirculation, in which the olefin reacts, preferably with temperature control.

Catalytic Composition

The effluent treated in the process according to the invention is thus obtained from a step of oligomerization of ethylene to olefin using a catalytic composition comprising an alkylaluminium halide and preferably a nickel precursor.

Preferably, the nickel precursor is chosen from nickel(II) chloride, nickel(II) chloride (dimethoxyethane), nickel(II) bromide, nickel(II) bromide (dimethoxyethane), nickel(II) fluoride, nickel(II) iodide, nickel(II) sulfate, nickel(II) carbonate, nickel(II) dimethylglyoxime, nickel(II) hydroxide, nickel(II) hydroxyacetate, nickel(II) oxalate, nickel(II) carboxylates, for instance nickel 2-ethylhexanoate, nickel(II) phenates, nickel(II) naphthenates, nickel(II) acetate, nickel (II) trifluoroacetate, nickel(II) triflate, nickel(II) stearate, nickel(II) formate, nickel(II) acetylacetonate, nickel(II) hexafluoroacetylacetonate, π-allylnickel(II) chloride, π-allylnickel(II) bromide, methallylnickel(II) chloride dimer, $\eta^3$-allylnickel(II) hexafluorophosphate, $\eta^3$-methallylnickel(II) hexafluorophosphate and 1,5-cyclooctadienylnickel(II), in their hydrated or non-hydrated form, taken alone or as a mixture.

Preferably, the nickel precursor is chosen from nickel(II) sulfate, nickel(II) carbonate, nickel(II) dimethylglyoxime, nickel(II) hydroxide, nickel(II) hydroxyacetate, nickel(II) oxalate, nickel(II) carboxylates, for instance nickel 2-ethylhexanoate, nickel(II) phenates, nickel(II) naphthenates, nickel(II) acetate, nickel(II) trifluoroacetate, nickel(II) triflate, nickel(II) acetylacetonate, nickel(II) hexafluoroacetylacetonate, π-allylnickel(II) chloride, π-allylnickel(II) bromide, methallylnickel(II) chloride dimer, $\eta^3$-allylnickel(II) hexafluorophosphate, $\eta^3$-methallylnickel(II) hexafluorophosphate and 1,5-cyclooctadienylnickel(II), in their hydrated or non-hydrated form, taken alone or as a mixture.

Advantageously, the alkylaluminium halide corresponds to the formula $[Al_m R^5_n X_{3-n}]_o$ in which $R^5$ is a linear or branched alkyl group, containing from 1 to 12 carbon atoms, X is a chlorine or bromine atom, and preferably a chlorine atom, and m is chosen from 1 and 2, n is chosen from 0, 1 and 2, o is chosen from 1 and 2.

When m is equal to 2, the groups $R^5$ may be identical or different.

Preferably, $R^5$ is chosen from a linear or branched alkyl group containing from 2 to 10 carbon atoms, preferably from 2 to 6 carbon atoms and preferably from 2 to 4 carbon atoms.

Preferably, $R^5$ is an alkyl group chosen from methyl, ethyl, propyl, isopropyl, n-butyl, tert-butyl, pentyl, hexyl, heptyl and octyl. Preferably, $R^5$ is an alkyl group chosen from ethyl, propyl, isopropyl, n-butyl and tert-butyl.

Advantageously, the alkylaluminium halide is chosen from the group formed by methylaluminium dichloride ($MeAlCl_2$), ethylaluminium dichloride ($EtAlCl_2$), ethylaluminium sesquichloride ($Et_3Al_2Cl_3$), diethylaluminium chloride ($Et_2AlCl$), diisobutylaluminium chloride ($iBu_2AlCl$) and isobutylaluminium dichloride ($iBuAlCl_2$), taken alone or as a mixture.

The mole ratio of the alkylaluminium halide to the nickel precursor, denoted as Al/Ni, is preferably greater than or equal to 5, more preferably greater than or equal to 6, and preferably less than or equal to 30, preferably less than or equal to 25, more preferably less than or equal to 20.

Advantageously, the catalytic composition may also comprise a ligand chosen from a phosphine.

In another embodiment, the catalytic composition comprises a ligand chosen from a phosphine of formula $PR^6R^7R^8$ in which the groups $R^6$, $R^7$ and $R^8$, which may be identical or different, optionally attached to each other, are chosen from substituted or unsubstituted aromatic groups optionally containing hetero-elements, and/or from cyclic or non-cyclic, substituted or unsubstituted alkyl groups optionally containing hetero-elements.

Advantageously according to the invention, the catalytic composition comprises at least one phosphine ligand of formula $PR^6R^7R^8$ in which the groups $R^6$, $R^7$ and $R^8$ are all identical.

The aromatic groups $R^6$, $R^7$ and $R^8$ of the phosphine ligand $PR^6R^7R^8$ are preferably chosen from the group formed by phenyl, o-tolyl, m-tolyl, p-tolyl, mesityl, 3,5-dimethylphenyl, 4-n-butylphenyl, 2-methoxyphenyl, 3-methoxyphenyl, 4-methoxyphenyl, 2-isopropoxyphenyl, 4-methoxy-3,5-dimethylphenyl, 3,5-di-tert-butyl-4-methoxyphenyl, 4-chlorophenyl, 3,5-bis(trifluoromethyl)phenyl, benzyl, naphthyl, bisnaphthyl, pyridyl, bisphenyl, furanyl and thiophenyl groups.

The alkyl groups $R^6$, $R^7$ and $R^8$ of the phosphine ligand $PR^6R^7R^8$ advantageously comprise 1 to 20 carbon atoms, preferably 2 to 15 carbon atoms, preferably between 3 and 10 carbon atoms. Preferably, the alkyl groups $R^6$, $R^7$ and $R^8$ of the phosphine ligand $PR^6R^7R^8$ are chosen from the group formed by methyl, ethyl, propyl, isopropyl, n-butyl, tert-butyl, cyclopentyl, cyclohexyl, benzyl and adamantyl groups.

Advantageously, the mole ratio between the phosphine ligand of formula $PR^6R^7R^8$ and the nickel precursor is between 5 and 25, preferably between 5 and 20, more preferably between 5 and 15. Preferably, this mole ratio is between 6 and 30, preferably between 6 and 25, more preferably between 6 and 20, even more preferably between 6 and 15, and even more preferentially between 7 and 14.

In a preferred embodiment, each constituent or mixture of constituents of the catalytic composition may be used in a solvent.

The solvent(s) are advantageously chosen from
ethers, alcohols, halogenated solvents and hydrocarbons, which are saturated or unsaturated, cyclic or non-cyclic, aromatic or non-aromatic, comprising between 1 and 20 carbon atoms, preferably between 1 and 15 carbon atoms and preferably between 4 and 15 carbon atoms,
ionic liquids.

Preferably, the solvent is chosen from pentane, hexane, cyclohexane, methylcyclohexane, heptane, butane or isobutane, 1,5-cyclooctadiene, benzene, toluene, ortho-xylene, mesitylene, ethylbenzene, diethyl ether, tetrahydrofuran, 1,4-dixoane, dichloromethane, dichloroethane, chlorobenzene, dichlorobenzene, methanol and ethanol, pure or as a mixture, and ionic liquids.

In the case where the solvent is an unsaturated hydrocarbon, it may be advantageously chosen from the products of the oligomerization reaction.

In the case where the solvent is an ionic liquid, it is advantageously chosen from N-butylpyridinium hexafluorophosphate, N-ethylpyridinium tetrafluoroborate, pyridinium fluorosulfonate, 3-butyl-1-methylimidazolium tetrafluoroborate, 3-butyl-1-methylimidazolium bis-trifluoromethanesulfonyl amide, triethylsulfonium bis-trifluoromethanesulfonyl amide, 3-butyl-1-methylimidazolium hexafluoroantimonate, 3-butyl-1-methylimidazolium hexafluorophosphate, 3-butyl-1-methylimidazolium trifluoroacetate, 3-butyl-1-methylimidazolium trifluoromethylsulfonate, trimethylphenylammonium hexafluorophosphate, tetrabutylphosphonium tetrafluoroborate, tetrabutylphosphonium chloride, N-butylpyridinium chloride, ethylpyridinium bromide, 3-butyl-1-methylimidazolium chloride, diethylpyrazolium chloride, pyridinium hydrochloride, trimethylphenylammonium chloride and butylmethylpyrrolidinium chloride.

Separation Step in an "Optional" Distillation Section

Typically, the olefins obtained from the ethylene oligomerization step have a higher molecular weight than the unreacted ethylene. In general, the unreacted ethylene has a lower boiling point than that of the oligomers obtained from the oligomerization step, such as 1-butene, 2-butenes, 1-hexene or 1-octene.

According to the invention, any separation means known to those skilled in the art which exploits these differences in volatility and in molecular weight between the products to be separated can be used in the separation step. Advantageously according to the invention, the separation means used are distillation columns of any type.

The process according to the invention optionally comprises a separation step advantageously comprising a distillation section. Preferably, according to the process of the invention, the gas fractions obtained from the thermal separation step, in particular comprising unconverted ethylene, the products formed and the solvent, are sent in gas/liquid mixed form to the distillation section.

The distillation section advantageously comprises at least three distillation columns, preferably at least four distillation columns. According to a preferred variant of the invention, the distillation section comprises four distillation columns.

The following examples illustrate the invention without limiting the scope thereof.

EXAMPLES

Implementation of the Oligomerization Step 93 mL of n-heptane are placed in a reactor, dried beforehand under vacuum and placed under an ethylene atmosphere, followed by 6 mL of a solution containing the nickel precursor Ni(2-ethylhexanoate)$_2$ (denoted as Ni(2-EH)$_2$, 40 µmol) and tricyclohexylphosphine (PCy$_3$) (400 µmol). Between 1 and 2 g of ethylene are then dissolved in the reactor, stirring is started and the temperature is set at 40° C. After degassing the reactor, the temperature is set at 45° C. (test temperature). 1 mL of a solution of ethylaluminium dichloride (600 µmop is then introduced. The reactor is set at the test pressure (2 MPa). Stirring is started, and the reaction is performed under pressure control, the ethylene feed making it possible to keep the pressure at the test pressure. After having reached the desired ethylene consumption, the ethylene feed is stopped. The liquid effluent is neutralized with a neutralizing system.

In the examples that follow, the gas effluents are quantified and qualified by gas chromatography (GC) and the liquid phases are weighed and qualified by GC.

Example 1: Thermal Separation Step with Two Vaporization Steps in Series (According to the Invention)

The neutralized effluent obtained on conclusion of the oligomerization step as described above is compressed to a pressure of 3.25 MPa and then partially vaporized by heating in a heat exchanger up to a temperature of 115° C. The gas fraction is then separated from the liquid fraction in a vessel. The gas fraction is sent to a distillation section and the liquid fraction is sent to a second flash.

The liquid fraction resulting from the first flash is expanded to a pressure of 1.35 MPa. Said expanded liquid fraction is then partially vaporized by heating in a heat exchanger up to a temperature of 117° C. The gas fraction is then separated from the liquid fraction in a vessel. The gas fraction is sent to the distillation section and the liquid phase comprising the neutralized catalyst is sent to an incinerator.

Table 1 below presents the conditions in the various steps and the composition of each stream. The final liquid effluent obtained from the second flash comprises the hetero-elements obtained from the catalytic system and from the inhibitor(s) (Ni, P, Al, Cl, O, N etc.) and also the associated organic part thereof.

It is seen that the use of a thermal separation step comprising two flashes in series makes it possible to separate the neutralized catalyst from the products of interest while maximizing the amount of olefins of interest (1-butene denoted B1 and 2-butene denoted B2) sent to a distillation section, which makes it possible to maximize the productivity of the oligomerization process.

Furthermore, no isomerization problems are observed during said thermal separation step, which makes it possible to send more than 99% of the butenes formed during the oligomerization step to the distillation section without degradation of the selectivity.

TABLE 1

Operating conditions and compositions of the streams entering and leaving the spent catalyst separation section

|  | Neutralized effluent | First step (Flash No. 1) | | Second step (Flash No. 2) | |
|---|---|---|---|---|---|
|  |  | gas fraction | liquid fraction | gas fraction | liquid fraction |
| Temperature (° C/) | 50 | 115 | | 117 | |
| Pressure (MPa) | 2.8 | 3.25 | | 1.35 | |
| Mass flow rate (kg/hour) |  |  |  |  |  |
| Ethylene | 6.95 | 6.0 | 0.95 | 0.94 | 0.003 |
| Ethylene per fraction/effluent (%) |  | 86.4 | 13.6 | 13.6 | 0.04 |
| 1-Butene | 33.1 | 22.2 | 10.9 | 10.8 | 0.14 |
| B1 per fraction/effluent (mass %) |  | 66.9 | 33.1 | 32.6 | 0.4 |
| 2-Butenes | 5.8 | 3.8 | 2.0 | 2.0 | 0.03 |
| B2 per fraction/effluent (mass %) |  | 64.9 | 35.1 | 34.6 | 0.5 |
| C6+ hydrocarbon | 5.2 | 2.0 | 3.1 | 2.9 | 0.26 |
| C6+ per fraction/effluent (mass %) |  | 39.1 | 60.9 | 55.9 | 5.0 |
| Neutralized catalyst | 0.020 | 0.000 | 0.020 | 0.000 | 0.020 |
| Neutralized catalyst per fraction/effluent (mass %) |  | 0.0 | 100.0 | 0.0 | 100.0 |
| Excess neutralizing system | 0.003 | 0.001 | 0.002 | 0.002 | 0.000 |
| Excess neutralizing system per fraction/effluent (mass %) |  | 20.5 | 79.5% | 65.8 | 13.7 |

Example 2: Thermal Separation Step with Three Vaporization Steps in Series (According to the Invention)

The neutralized effluent obtained on conclusion of the oligomerization step as described above is compressed to a pressure of 3.25 MPa and then partially vaporized by heating in a heat exchanger up to a temperature of 115° C. The gas fraction is then separated from the liquid fraction in a vessel. The gas fraction is sent to a distillation section and the liquid fraction is sent to a second flash.

The liquid fraction resulting from the first flash is expanded to a pressure of 1.3 MPa. Said expanded liquid fraction is then partially vaporized by heating in a heat exchanger up to a temperature of 107° C. The gas fraction is then separated from the liquid fraction in a vessel. The gas fraction is sent to the distillation section and the liquid fraction is sent to a third flash.

The liquid fraction resulting from the second flash is expanded to a pressure of 0.5 MPa. Said expanded liquid fraction is then vaporized by heating in a heat exchanger up to a temperature of 98° C.

Table 2 below presents the conditions in the various steps and the composition of each stream. The final liquid effluent obtained from the third flash comprises the hetero-elements obtained from the catalytic system and from the inhibitor(s) (Ni, P, Al, Cl, O, N etc.) and also the associated organic part thereof.

Advantageously, in this separation embodiment, no isomerization of the desired olefins is observed, which makes it possible to maximize the recovery of the products of interest.

TABLE 2

Operating conditions and compositions of the streams entering and leaving the spent catalyst separation section

|  | Inlet | First step (Flash No. 1) | | Second step (Flash No. 2) | | Third step (Flash No. 3) | |
|---|---|---|---|---|---|---|---|
|  |  | gas fraction | liquid fraction | gas fraction | liquid fraction | gas fraction | liquid fraction |
| Temperature (° C.) | 50 | 115 | | 107 | | 98 | |
| Pressure (MPa) | 2.8 | 3.25 | | 1.3 | | 5.2 | |
| Mass flow rate (kg/hour) |  |  |  |  |  |  |  |
| Ethylene | 6.9 | 6.0 | 0.95 | 0.93 | 0.013 | 0.01 | 0.001 |
| Ethylene per fraction/effluent (mass %) |  | 86.4 | 13.6 | 13.4 | 0.2 | 0.2 | 0.01 |
| 1-Butene | 33.1 | 22.2 | 10.9 | 10.2 | 0.7 | 0.5 | 0.2 |
| B1 per fraction/effluent (mass %) |  | 67.0 | 33.0 | 30.9 | 2.1 | 1.6 | 0.5 |
| 2-Butenes | 5.8 | 3.8 | 2.0 | 1.9 | 0.15 | 0.1 | 0.04 |
| B2 per fraction/effluent (mass %) |  | 64.9 | 35.1 | 32.6 | 2.5 | 1.9 | 0.7 |
| C6+ hydrocarbon | 5.2 | 2.0 | 3.1 | 2.2 | 0.94 | 0.2 | 0.69 |
| C6+ per fraction/effluent (mass %) |  | 39.1 | 60.9 | 42.7 | 18.2 | 4.8 | 13.4 |
| Spent catalyst | 0.020 | 0.000 | 0.020 | 0.000 | 0.020 | 0.000 | 0.020 |

TABLE 2-continued

Operating conditions and compositions of the streams entering
and leaving the spent catalyst separation section

|  | Inlet | First step (Flash No. 1) | | Second step (Flash No. 2) | | Third step (Flash No. 3) | |
| --- | --- | --- | --- | --- | --- | --- | --- |
|  |  | gas fraction | liquid fraction | gas fraction | liquid fraction | gas fraction | liquid fraction |
| Catalyst per fraction/effluent (mass %) |  | 0.0 | 100.0 | 0.0 | 100.0 | 0.0 | 100.0 |
| Excess inhibitor | 0.003 | 0.001 | 0.002 | 0.001 | 0.001 | 0.000 | 0.001 |
| Excess inhibitor per fraction/effluent (mass %) |  | 20.5 | 79.5 | 35.5 | 44.1 | 4.8 | 39.3 |

Example 3: Neutralization Step

Neutralization Step

The effluent obtained on conclusion of the oligomerization step as described above is placed in contact with the neutralizing system comprising 2-ethylhexylamine and 2-ethylhexanol, at a temperature of 50° C. and at various mole ratios of the amine and the alcohol to the ethylaluminium dichloride (denoted as Al). The results obtained are shown in the table below. The isomerization is monitored by GC.

TABLE 3

Conditions during the neutralization step

| Inlet | Chlorine content (ppm by weight) in the neutralized effluent leaving the oligomerization step | Neutralizing system | Neutralizing system/ Al mole ratio | Isomerization at 100° C. | Corrosion |
| --- | --- | --- | --- | --- | --- |
| 1 | 270 | 2-Ethylhexylamine | 1.1 | Yes | No |
| 2 | 270 | 2-Ethylhexylamine | 4.0 | Yes | No |
| 3 | 270 | 2-Ethylhexanol | 1.1 | nd | Yes |
| 4 | 270 | 2-Ethylhexanol | 4.0 | nd | Yes |
| 5 | 270 | 2-Ethylhexylamine + 2-ethylhexanol | 2.7 1.1 | nd | No |
| 6 | 40 | 2-Ethylhexylamine + 2-ethylhexanol | 2.7 1.1 | nd | No |
| 97 | 60 | 2-Ethylhexylamine + 2-ethylhexanol | 4.0 4.0 | nd | No | nd: not detected

Thus, the neutralizing system according to the invention, and preferably the neutralizing system comprising an alcohol and an amine, makes it possible to ensure the neutralization of the mixture while at the same time maintaining the selectivity towards desired olefins obtained from the oligomerization step and while preventing the corrosion problems associated with the presence of chlorine.

The invention claimed is:

1. A process for treating an effluent obtained from a dimerization step having selectivity for 1-butene, the process comprising a step of neutralizing said effluent obtained from a dimerization step to deactivate a catalytic composition followed by a step of thermal separation of the neutralized effluent, comprising:
   a first vaporization step performed at a pressure of between 2.0 and 5.0 MPa and at a temperature of between 90° C. and 130° C., to obtain a first liquid fraction sent to a second vaporization step, and a first gas fraction,
   wherein said second vaporization step is performed at a pressure of between 0.5 and 3.0 MPa and at a temperature of between 90° C. and 130° C., to obtain a second liquid fraction and a second gas fraction;
   wherein the pressure of the first vaporization step is higher than the pressure of the second vaporization step,
   wherein the thermal separation step further comprises a third vaporization step into which the second liquid fraction obtained from the second vaporization step is sent, wherein said third vaporization step is performed at a pressure of between 0.3 and 1.2 MPa and at a temperature of between 8° and 140° C., wherein a third liquid fraction and a third gas fraction are obtained;
   wherein the pressure of the second vaporization step is higher than the pressure of the third vaporization step; and
   wherein the step of neutralizing the effluent obtained from the dimerization step is performed by placing said effluent in contact with a neutralizing system comprising an alcohol of formula $R^1OH$ and an amine of formula $NR^2R^3R^4$
   wherein
   $R^1$ is a linear a group containing 2 to 20 carbon atoms or a branch alkyl group containing 3 to 20 carbon atoms, or an aryl group containing 5 to 30 carbon atoms, $R^2$, $R^3$ and $R^4$, which may be identical or different, are independently a hydrogen, or a linear alkyl group containing 1 to 20 carbon atoms and optionally substituted with an $NH_2$ group, or a branched alkyl group containing 3 to 20 carbon atoms and optionally substituted with an $NH_2$ group.

2. The process according to claim 1, wherein the first vaporization step is performed between 2.0 MPa and 4.5 MPa.

3. The process according to claim 1, wherein the second vaporization step is performed between 0.8 MPa and 3.0 MPa.

4. The process according to claim 1, wherein the third vaporization step is performed between 0.4 MPa and 1.0 MPa.

5. The process according to claim 4, wherein the third vaporization step is performed at a temperature of between 80° C. and 130° C.

6. The process according to claim 1, wherein the first step and/or the second step and/or the third step of thermal separation are performed by a flash vessel, optionally coupled with a heat exchanger.

7. The process according to claim 1, wherein the first gas fraction obtained from the first vaporization step and/or the second gas fraction obtained from the second vaporization step and/or the third gas fraction obtained from the third vaporization step are liquefied at a pressure of between 2.0 and 5.0 MPa.

8. The process according to claim 7, wherein a temperature for liquefying the first, second and/or third gas fractions is between 0 and 60° C.

9. The process according to claim 1, wherein the dimerization step from which the effluent has been obtained used a catalytic composition comprising an alkylaluminium halide and optionally a nickel precursor.

10. The process according to claim 9, wherein the alkylaluminium halide corresponds to formula

wherein $R^5$, $R^6$, $R^7$ and $R^8$ are, each independently, a linear alkyl group containing from 1 to 12 carbon atoms or a branched alkyl group containing from 3 to 12 carbon atoms, X is either a chlorine atom or a bromine atom, oa=1 or 2, ob=0 or 1, the sum of oa and ob is 1 or 2, ma=1 or 2, na1=1 or 2, na2=0 or 1, na3=1 or 2, if ma=1, the sum of na1, na2 and na3 is 3, if ma=2, the sum of na1, na2 and na3 is 2, mb=1 or 2, nb1=1 or 2, nb2=0 or 1, nb3=1 or 2, if mb=1, the sum of nb1, nb2 and nb3 is 3, and if mb=2, the sum of nb1, nb2 and nb3 is 2.

11. The process according to claim 9, wherein the effluent obtained from the dimerization step has a content of alkylaluminium halide of between 0.01 and 100 000 ppm by weight.

12. The process according to claim 1, wherein a temperature at which the neutralizing system is placed in contact with the effluent obtained from the dimerization step is the same as a temperature at which said oligomerization step takes place.

13. The process according to claim 1, wherein the first vaporization step is performed between 95° C. and 120° C.

14. The process according to claim 13, wherein the second vaporization step is performed between 95° C. and 125° C.

15. The process according to claim 1, wherein the second vaporization step is performed between 95° C. and 125° C.

16. The process according to claim 1, wherein a mole ratio of the amine of the formula $NR^2R^3R^4$ to the alcohol of the formula $R^1OH$ is between 1.1 and 20.

17. The process according to claim 1, wherein a mole ratio of the amine of the formula $NR^2R^3R^4$ to the alcohol of the formula $R^1OH$ is between 2 and 10.

18. The process according to claim 1, wherein a mole ratio of the amine of the formula $NR^2R^3R^4$ to the alcohol of the formula $R^1OH$ is between 2.2 and 5.0.

19. The process according to claim 1, wherein the amine of formula $NR^2R^3R^4$ is 2-Ethylhexylamine and the alcohol of formula $R^1OH$ is 2-ethylhexanol.

20. A process for treating an effluent obtained from a dimerization step having selectivity for 1-butene, the process comprising a step of neutralizing said effluent obtained from a dimerization step to deactivate a catalytic composition followed by a step of thermal separation of the neutralized effluent, comprising:

a first vaporization step performed at a pressure of between 2.0 and 5.0 MPa and at a temperature of between 90° C. and 130° C., to obtain a first liquid fraction sent to a second vaporization step, and a first gas fraction, wherein said second vaporization step is performed at a pressure of between 0.5 and 3.0 MPa and at a temperature of between 90° C. and 130° C., to obtain a second liquid fraction and a second gas fraction;

wherein the pressure of the first vaporization step is higher than the pressure of the second vaporization step, wherein the thermal separation step further comprises a third vaporization step into which the second liquid fraction obtained from the second vaporization step is sent, wherein said third vaporization step is performed at a pressure of between 0.3 and 1.2 MPa and at a temperature of between 80 and 140° C., wherein a third liquid fraction and a third gas fraction are obtained;

wherein the pressure of the second vaporization step is higher than the pressure of the third vaporization step; and wherein the step of neutralizing the effluent obtained from the dimerization step is performed by placing said effluent in contact with a neutralizing system comprising an alcohol of formula $R^1OH$ and an amine of formula $NR^2R^3R^4$ wherein $R^1$ is a linear alkyl group containing 2 to 20 carbon atoms or a branched alkyl group containing 3 to 20 carbon atoms, or an aryl group containing 5 to 30 carbon atoms, $R^2$, $R^3$ and $R^4$, which may be identical or different, are independently a hydrogen, or a linear alkyl group containing 1 to 20 carbon atoms and optionally substituted with an $NH_2$ group, or a branched alkyl group containing 3 to 20 carbon atoms and optionally substituted with an $NH_2$ group, wherein a mole ratio of the amine of the formula $NR^2R^3R^4$ to the alcohol of the formula $R^1OH$ is between 0.5 and 100.

* * * * *